(12) United States Patent
Elghazzawi et al.

(10) Patent No.: US 10,258,806 B2
(45) Date of Patent: *Apr. 16, 2019

(54) MEDICAL EQUIPMENT SERVICING

(71) Applicant: ZOLL Medical Corporation, Chelmsford, MA (US)

(72) Inventors: Ziad F Elghazzawi, Newton, MA (US); Ian B Durrant, Arlington, MA (US); Henry Clay Constantine, III, Rochester, NY (US)

(73) Assignee: ZOLL Medical Corporation, Chelmsford, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/957,946

(22) Filed: Apr. 20, 2018

(65) Prior Publication Data
US 2018/0236252 A1    Aug. 23, 2018

Related U.S. Application Data

(63) Continuation of application No. 15/624,779, filed on Jun. 16, 2017, now Pat. No. 9,974,969, which is a (Continued)

(51) Int. Cl.
*A61N 1/39* (2006.01)
*G06F 17/30* (2006.01)
(Continued)

(52) U.S. Cl.
CPC .............. *A61N 1/3931* (2013.01); *A61N 1/39* (2013.01); *G06F 17/30312* (2013.01);
(Continued)

(58) Field of Classification Search
CPC ................................ A61N 1/39; A61N 1/3931
(Continued)

(56) References Cited

U.S. PATENT DOCUMENTS 5,919,212 A    7/1999  Olson
6,088,616 A    7/2000  Olson
(Continued)

FOREIGN PATENT DOCUMENTS

WO    2009136259 A2    11/2009

*Primary Examiner* — Carl H Layno
*Assistant Examiner* — Jon Eric C Morales
(74) *Attorney, Agent, or Firm* — ZOLL Medical Corporation

(57) ABSTRACT

A medical equipment management system is described. The medical equipment management system includes a database including software for a plurality of external defibrillators, the software including at least one of new software and updated software and a computer located remotely from the plurality of external defibrillators and configured to be communicatively coupled to the plurality of external defibrillators and to receive a login request from a administrator, based on the login request, determine, from amongst the plurality of external defibrillators in the database, a set of external defibrillators associated with the administrator, determine whether the software stored in the database is relevant to the set of external defibrillators associated with the administrator, and send the relevant software to the set of external defibrillators associated with the administrator.

29 Claims, 7 Drawing Sheets

Related U.S. Application Data continuation of application No. 14/823,715, filed on Aug. 11, 2015, now Pat. No. 9,814,893, which is a continuation of application No. 13/558,957, filed on Jul. 26, 2012, now Pat. No. 9,220,912.

(51) Int. Cl.
*G16H 40/40* (2018.01)
*G06F 19/00* (2018.01)
*H04W 64/00* (2009.01)

(52) U.S. Cl.
CPC ........ *G06F 17/30345* (2013.01); *G06F 19/00* (2013.01); *G16H 40/40* (2018.01); *H04W 64/00* (2013.01)

(58) Field of Classification Search
USPC .......................................... 600/300, 485, 561
See application file for complete search history.

(56) References Cited

U.S. PATENT DOCUMENTS

| | | | |
|---|---|---|---|
| 6,370,428 B1 | 4/2002 | Snyder | |
| 6,397,104 B1 | 5/2002 | Miller | |
| 6,492,581 B1 | 12/2002 | Bradbury | |
| 6,747,556 B2 | 6/2004 | Medema | |
| 6,754,526 B2 | 6/2004 | Daynes | |
| 6,813,517 B2 | 11/2004 | Daynes | |
| 6,937,150 B2 | 8/2005 | Medema | |
| 7,672,720 B2 | 3/2010 | Heath | |
| 7,769,465 B2 | 8/2010 | Matos | |
| 7,805,190 B2 | 9/2010 | Chapman | |
| 7,937,146 B2 | 5/2011 | Banville | |
| 7,979,378 B2 | 7/2011 | West | |
| 8,081,071 B1 | 12/2011 | Vaisnys | |
| 9,220,912 B2 * | 12/2015 | Elghazzawi | A61N 1/39 |
| 2003/0028219 A1 | 2/2003 | Powers | |
| 2003/0212311 A1 | 11/2003 | Nova | |
| 2003/0212438 A1 | 11/2003 | Nova | |
| 2004/0214148 A1 | 10/2004 | Salvino | |
| 2005/0015115 A1 | 1/2005 | Sullivan | |
| 2006/0030891 A1 | 2/2006 | Saltzstein | |
| 2006/0084043 A1 | 4/2006 | Weaver | |
| 2007/0108274 A1 | 5/2007 | Boardman | |
| 2007/0185545 A1 | 8/2007 | Duke | |
| 2008/0138778 A1 | 6/2008 | Eggert | |
| 2009/0222539 A1 | 9/2009 | Lewis | |
| 2010/0250643 A1 | 9/2010 | Savage | |
| 2011/0057082 A1 | 3/2011 | West | |
| 2012/0081230 A1 | 4/2012 | Sullivan | |

* cited by examiner

MEDICAL EQUIPMENT SERVICING

TECHNICAL FIELD

This application is a continuation under 35 USC § 120 to U.S. patent application Ser. No. 15/624,779, filed on Jun. 16, 2017 and issued as U.S. Pat. No. 9,974,969, which is a continuation of U.S. patent application Ser. No. 14/823,715, filed on Aug. 11, 2015 and issued as U.S. Pat. No. 9,814,893 which is a continuation of U.S. patent application Ser. No. 13/558,957, filed Jul. 26, 2012 and issued as U.S. Pat. No. 9,220,912. All subject matter set forth in the above referenced applications is hereby incorporated by reference in its entirety into the present application as if fully set forth herein.

Systems and techniques for centralized management and servicing of medical equipment such as automated external defibrillators (AEDs) are described 5 herein.

BACKGROUND

Sudden health problems such as sudden cardiac arrest and injuries caused by accidents kill thousands of people and cause permanent injury every year. Fast and competent care can be essential to positive outcomes in such situations. For example, it is said that the chance of surviving a sudden cardiac arrest falls by ten percent for every minute in delaying effective treatment.

Emergency events like sudden cardiac arrests and accidents are generally responded to by organized emergency response units, such as ambulance or fire crews, and by laypeople who are immediately around the events so that they personally witness or offer assistance for the events.

SUMMARY

In some aspects, a method includes receiving status updates from multiple automated external defibrillators, receiving, from a user, a request to access status information, and sending, to the user, summary level status information for at least some of the multiple automated external defibrillators, the summary level status information being grouped based on a measure of geographic proximity of the multiple automated external defibrillators.

Other embodiments of this aspect include corresponding systems, apparatus, and computer programs recorded on one or more computer storage devices, each configured to perform the actions of the methods. A system of one or more computers can be configured to perform particular actions by virtue of having software, firmware, hardware, or a combination of them installed on the system that in operation cause the system to perform the actions. One or more computer programs can be configured to perform particular actions by virtue of including instructions that, when executed by data processing apparatus, cause the apparatus to perform the actions.

Other features and advantages of the invention will be apparent from the drawings, detailed description, and claims.

DETAILED DESCRIPTION

Figure 1:
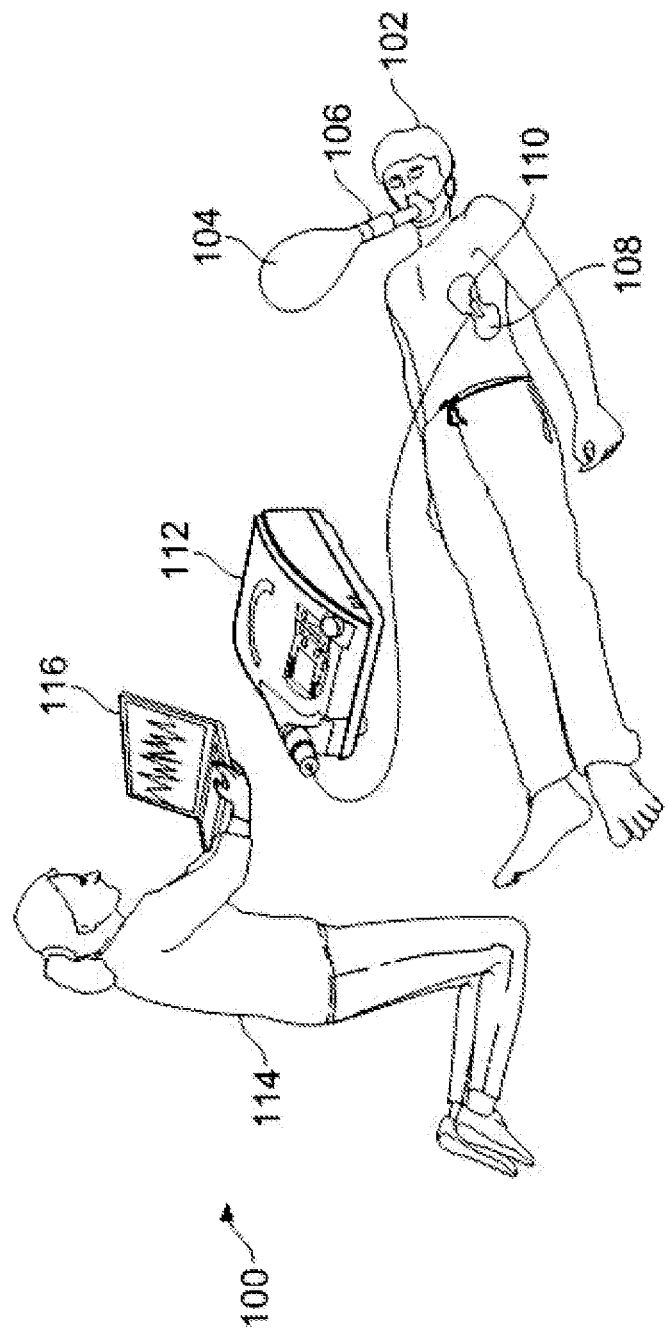
FIG. 1 is a schematic diagram of a system for responding to an emergency medical condition according to an example embodiment of the invention.

FIG. 1 shows a system 100 for responding to an emergency medical condition of a subject 102. In general, system 100 includes various portable devices for monitoring on-site care given to the subject 102 of the emergency situation. A rescuer 114 in this example is interacting with a computing device in the form of a laptop computer 116 that includes a graphical display by which to report information to the rescuer 114, and may have an input mechanism such as a keyboard or a touchscreen by which the rescuer 114 may enter data into the system 100. Separately, a portable defibrillator 112 is shown in a deployed state and is connected to the subject 102. In addition to providing defibrillation, the defibrillator 112 may serve as a patient monitor via a variety of sensors or sensor packages. For example, as shown here, electrodes 108 connected to the defibrillator 112 have been applied to the subject 102 so that electrical shocking pulses may be provided to the electrodes in an effort to defibrillate the subject 102, and electrocardiogram (ECG) signals may be read from the subject 102. Further examples of use of the portable defibrillator are described, for example, in Ser. No. 13/398,280 filed on Feb. 16, 2012 and entitled "Coordinated Resuscitation Perfusion Support", the contents of which are hereby incorporated by reference.

The defibrillator 112 may include an accelerometer assembly 110 configured to identify a vertical displacement caused by CPR compressions and provide feedback to the rescuer based on the measured displacements. The defibrillator can additionally be provided with a ventilation bag 104 that includes an airflow sensor 106 to identify a rate at which ventilation is occurring with the subject. The defibrillator 112 may communicate through a short range wireless data connection with the laptop 116 to provide to the laptop 116 status information, such as information received through the electrode assembly 108, including ECG information for the subject 102. Also, the defibrillator 112 can provide information to the rescuer 114 about the performance of chest compressions, such as depth and rate information for the chest compressions. The defibrillator operates according to a set of configurations stored on the defibrillator. The configurations can include a language setting, a CPR rate setting, a CPR depth setting, a shock voltage, and a shock wave form.

In order for a defibrillator, such as defibrillator 112, to be useful during a medical emergency, the defibrillator must be charged and functional when the device is needed. In order to ensure the defibrillators are functional, regular servicing is needed. For example, batteries must be replaced when they no longer store adequate charge to power the defibrillator, electrodes may need to be replaced to ensure the electrodes will function appropriately, and the like. Additionally, over time software for the defibrillators may be updated based on enhancements or changes to protocols and/or configurations for the defibrillator may be modified based on changes in various protocols. As such, after defibrillator is purchased and installed at a location regular servicing is needed to ensure that the device will be available and functional when needed.

Figure 2:
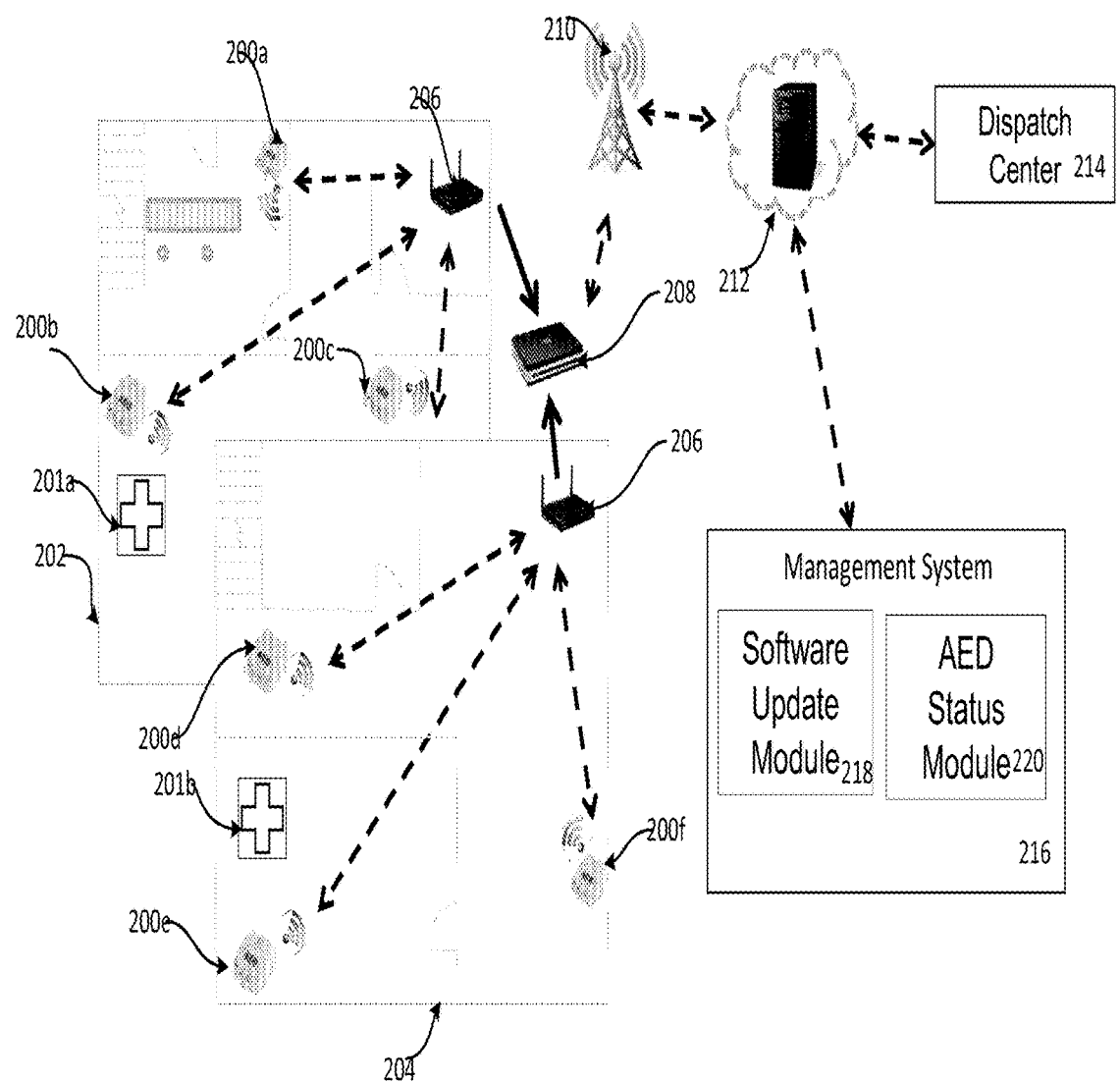
FIG. 2 is a block diagram of a system for managing medical equipment according to an example embodiment of the invention.

FIG. 2 shows a system for communication between medical equipment and a dispatch center 214 and a medical equipment management system 216. Medical equipment, e.g., defibrillation devices 200a-f and first-aid units 201a-b are communicatively coupled to the dispatch center 214 and the medical equipment management system 216.

Communications between the dispatch center 214 and the devices 200a-f and 201a-b can be used to alert rescue services upon activation of one of the devices and/or to communicate with a rescuer when one of the devices 200a-f is in use. Such communication between defibrillators and a dispatch center 214 is described, for example, in U.S. patent application Ser. No. 12/946,843, filed on Nov. 15, 2010, and entitled Community-Based Response System, the contents of which is hereby incorporated by reference in its entirety.

Communications between the medical equipment management system 216 and the medical equipment (e.g., defibrillation devices 200a-f and first aid units 201a-b) can provide centralized servicing of the medical equipment. The medical equipment management system 216 can include a status module 220 and a software update module 218. The status module 220 receives status information from medical equipment communicatively coupled to the medical equipment management system 216, and provides centralized access to this information as described in more detail below. The software update module 218 can include information about the software and/or configurations currently stored on various medical equipment and new software and/or configurations available for the medical equipment. The software update module 218 can additionally send (e.g., push) updates to a particular piece of medical equipment to change or update the software and/or configurations of the medical equipment.

More particularly, as shown in FIG. 2, multiple pieces of medical equipment such as defibrillation devices 200a-f and first aid units 201a-b can be located in various physical locations. A particular building or area may include multiple defibrillation devices or other pieces of medical equipment. For example, building 202 includes defibrillation devices 200a, 200b, and 200c and first aid unit 201a. Each of these devices can be communicatively coupled to the management center 216. For example, defibrillation devices 200a, 200b, and 200c and first aid unit 201a can include a transmitter in communication with a wireless router 206. The wireless router 206 can send messages received from the defibrillation devices 200a, 200b, and 200c and first aid unit 201a to an external router 208 and the router can relay the messages to a remotely located server 212 via a cellular network 210. Messages sent from defibrillation devices 200a, 200b, and 200c and first aid unit 201a can include information about the status of the medical equipment. For example, the messages can include information such as battery charging level, date of last servicing, error indications, electrodes or other component expirations, supply shortages and the like. These messages are relayed to the medical equipment and management system 216. Thus, the medical equipment provides messages indicative of their status to a medical equipment management system 216 and the medical equipment management system 216 can provide a centralized location for a device administrator to access status information for multiple disparately located devices. Centralized storage and access to information about the status of different pieces of medical equipment such as defibrillation devices can reduce the time and cost associated with servicing medical equipment because the administrator does not need to physically go to the devices to check their status. Additionally, servicing calls can more easily be grouped based on location because the administrator can identify devices in need of servicing in proximity to one another.

Figure 3A:
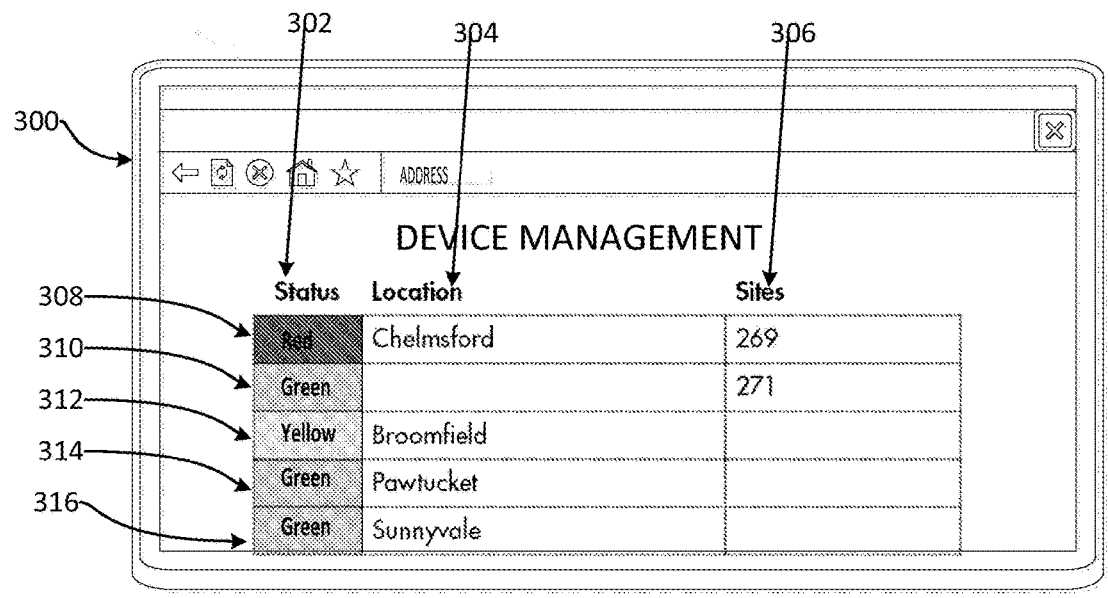
FIGS. 3A-B show exemplary screen shots for medical equipment management.
Figure 3B:
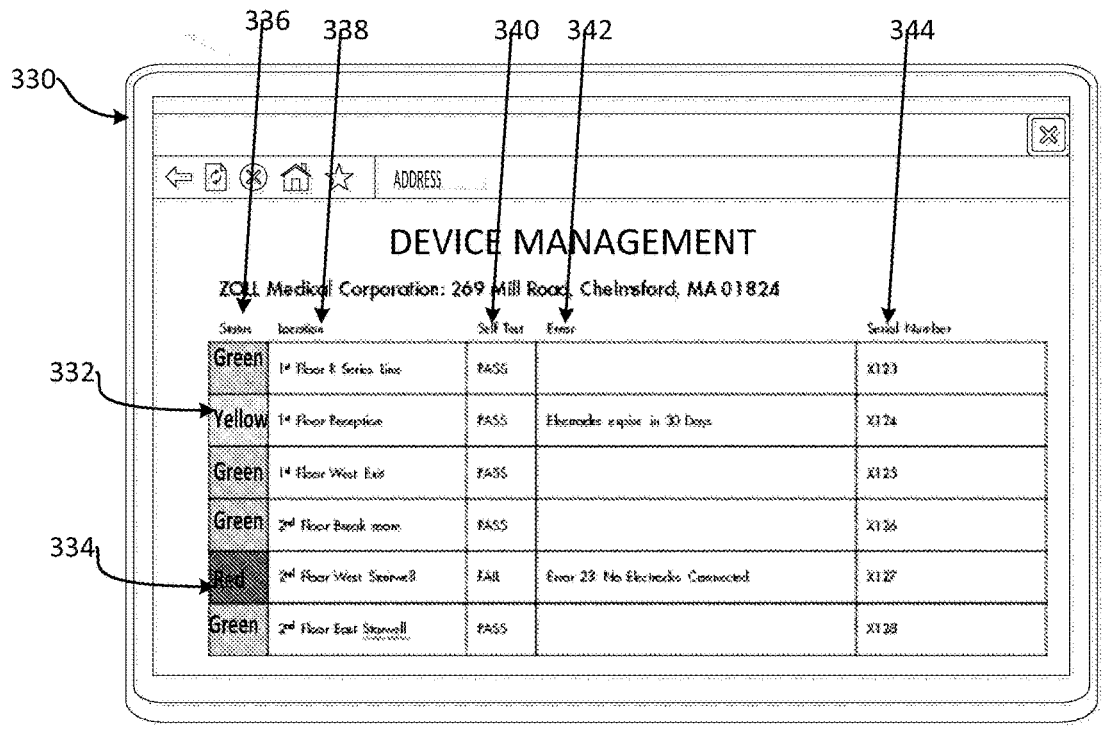

FIGS. 3A-B show exemplary screen shots for providing information about the status of medical equipment to an administrator of the medical equipment. As shown in FIG. 3A, a user interface 300 includes a device management status table. The status table includes a status column 302 that displays summary level status information for medical equipment grouped by location. The location is displayed in location column 304 and, if multiple sites exist for a particular location, a site number is displayed in site column 306. Thus, user interface 300 provides summary level information about medical equipment grouped by location (e.g., as shown in rows 308, 310, 312, 314, 316). For example, if multiple units of medical equipment exist at any particular geographic area (e.g., multiple devices in a particular building, such as building 202 and FIG. 2), the status information relays a summarized status of the medical equipment for the selected area. In some examples, the status displayed is the lowest status (e.g., worst) of all of the medical equipment associated with the location. For example, if a location included 10 medical equipment with one being nonfunctional, two being functional but in need of routine servicing, and seven devices that are fully functional, the status displayed in status column 302 would indicate a nonfunctional device.

The status can be displayed as color-coded icons associated with each piece of medical equipment where the color coding is indicative of the status. For example as shown in FIG. 3A, the entries in the status column 302 can be color-coded to indicate whether the equipment is fully functional. In one particular example, a green color coding of the icon could be representative of equipment that has recently been tested and is fully functional, a red color coding can be representative of equipment that is not fully functional, and a yellow color coding could be representative of equipment that has not recently been tested but was previously functional at the time of the last test and/or representative of equipment that is in need of routine servicing. In the particular example shown in row 308, devices associated with the Chelmsford location are color-coded as red to indicate that one or more of the associated medical devices in that location is not functional.

FIG. 3B shows a user interface 330 for providing device level status information for medical equipment. User interface 330 can be displayed based on a user's selection of a particular grouped location from user interface 300. For example, clicking on a link in row 308 in user interface 300 can produce user interface 330, which provides device level status information for the devices at the selected location (e.g., the Chelmsford location). The device level status information shown in user interface 330 can include a status column 336, location column 338, self-test results column 340, error identification column 342, and serial number column 344. The status column 336 can include status information for a particular device. The status information can be similar to the status information described above. The location column 338 includes details of the location for the particular piece of medical equipment. For example, the location could include an address and/or a location within a building. This location is specific to the particular device as opposed to being a generalized group location as shown in FIG. 3A. The self-test results column 340 includes information about whether the medical equipment has passed or failed a self-test and/or an option to initiate a test of the device. Additionally, in some examples, the self-test results column 340 would include information about the date of the most recent self-test. The error column 342 includes information about why a device has failed a self-test and/or servicing needed for the device. The serial number column 344 includes a serial number for the medical equipment such that the medical equipment can be identified by the administrator.

Allowing an administrator to view status information for each of the devices at a particular location can provide the administrator with information about why devices are not functioning and/or what issues could be addressed during a single servicing call. For example, if an administrator is making a service call to the Chelmsford location to service the nonfunctional device, the administrator can additionally view the status of other devices and service those devices at the same time. In the particular example of FIG. 3B, while servicing the device on the second floor west stairwell (e.g., shown in row 334) the administrator could additionally replace the electrodes in the device on the first floor reception (e.g., as shown in row 332). Additionally, identification of an error (e.g., shown in column 336) that has resulted in the status of the medical equipment can help the administrator to prepare for the needed servicing.

In some examples, the location grouping (e.g., as shown in FIG. 3A) can be modified by a user to change the grouping to include devices located within a larger or smaller geographic area. For example, a user could select from viewing location based on city, zip code, building, neighborhood, company, or user-defined geographic regions. Allowing a user to select and change the size of the location used to group medical equipment when displaying their status can enable an administrator to more effectively service the devices. For example, in a major metropolitan area medical equipment such as defibrillators could be densely located such that displaying status information on a citywide level would provide little assistance to an administrator when trying to plan for servicing calls (e.g., displaying defibrillators in Boston could result in thousands of defibrillators). In such a situation, the administrator could narrow the geographic extent used to group the medical equipment, such that fewer medical equipment are associated with each location.

Figure 4:
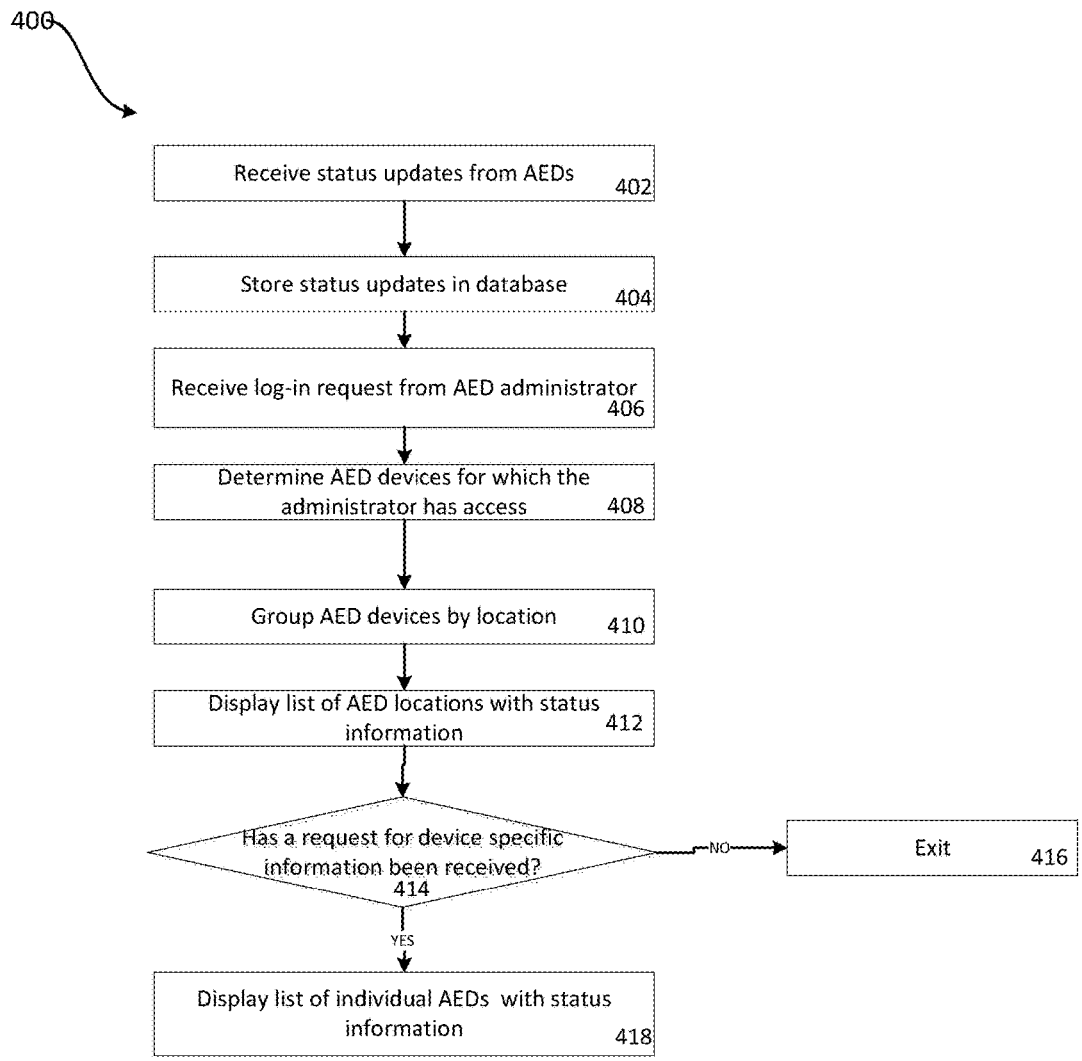
FIG. 4 is a flow chart of a process for providing status information about medical equipment according to an example embodiment of the invention.

FIG. 4 is a flow chart of a process 400 for providing status information about automated external defibrillators (AEDs). While process 400 is described herein as providing status information about AEDs, this process could additionally and/or alternatively be applied to other types of medical equipment. AEDs send status information to a medical equipment management system 216. The medical equipment management system 216 receives the status updates from the AEDs (402). The medical equipment management system 216 stores the status updates in a centralized database (404). For example, the medical equipment management center can include a database of AEDs and information about the status associated with each AED can be updated based on the received status updates.

The medical equipment management system 216 receives a login request from an AED administrator (406). Based on the authentication of the administrator, the medical equipment management system 216 determines AED devices for which the administrator should be granted access (408). For example, in the database that includes the information about the AEDs and their status, each AED may be associated with one or more administrators who are allowed access to the status of the AEDs. After determining a set of AEDs for which the user has access, the medical equipment management system 216 groups the AEDs by location (410). For example, the medical equipment management system 216 can group the AEDs by city, neighborhood, building, or another measure of geographic proximity. The medical equipment management system 216 displays the list of AED locations and status information for each location to the user (412). As noted above, the status information is indicative of a status for the multiple devices associated with in the location. For example, the status information can display the lowest or worst status of all devices within the location. In another example, the status information could include a percentage of devices included in the group for the location having each of a plurality of different statuses. For example, if the system provided three statuses of red, yellow, and green (as described above), then the system could display the percentage of AEDs falling into each of the color-coded categories.

While location level summary information about the status of the AEDs included in the location can be beneficial, and some situations an administrator may desire to see information on a device level rather than a location level. The medical equipment management system 216 determines whether a request for device specific information has been received (414). For example, referring back to FIG. 3A, a user can request to view device specific information for a location by clicking on one of the rows in the displayed status information table. In response to receiving a request for device specific information, the medical equipment management system displays a list of individual AEDs and their associated status information (418). For example, device level information such as the information shown in FIG. 3B can be provided to the user. If a request for the device level information is not received, the system exits the process (416).

As noted above, over time software for the defibrillators or other medical equipment may be updated based on enhancements or changes to protocols and/or configurations for the defibrillator may be modified. The medical equipment management system 216 can provide a centralized access and management tool for updating software and/or configurations for remotely located medical equipment such as AEDs. By providing a central server that has information about currently stored software and configurations and the ability to push software and configuration changes to remotely located medical equipment, the software and configurations for medical equipment can more easily be kept up to date as changes are promulgated.

Figure 5:
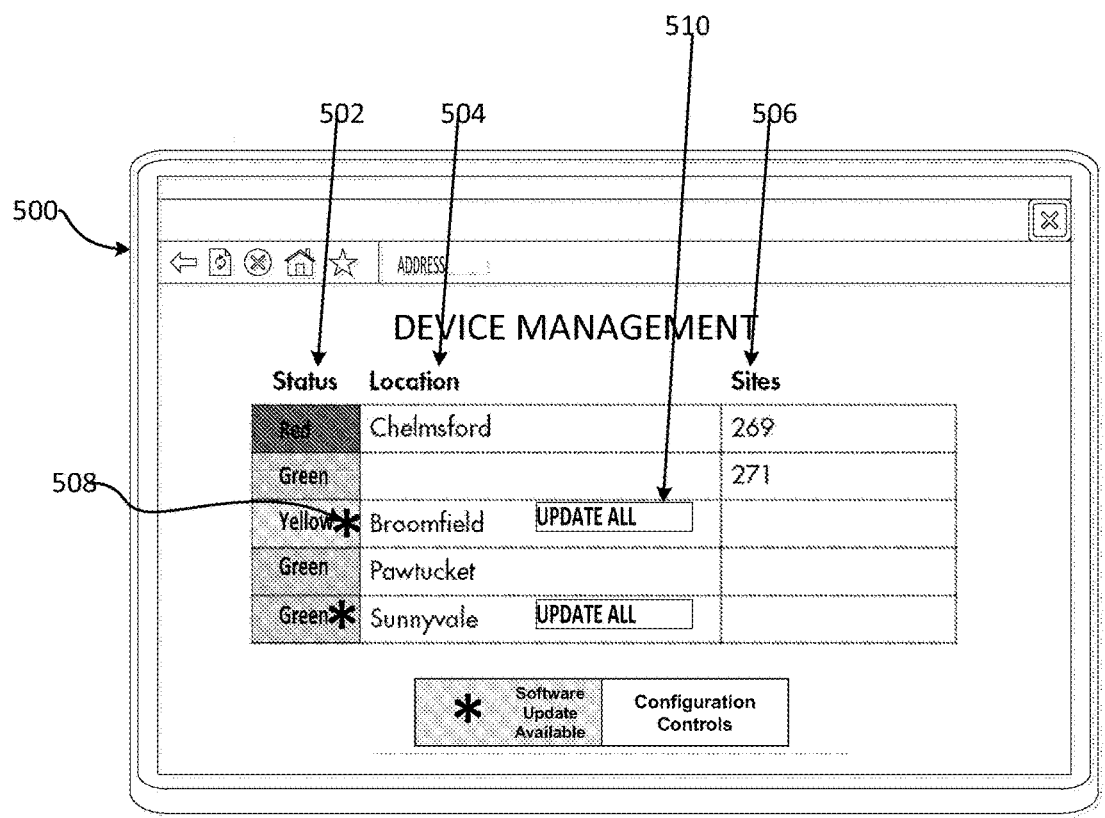
FIG. 5 is an exemplary screen shot for medical equipment management.

FIG. 5 is an exemplary screen shot for identifying medical equipment for which the software update and/or configuration update is available, and sending information to update the medical device. Similar to the device management user interface 300 shown in FIG. 3A, user interface 500 includes a table with a status column 502, location column 504 and site column 506. In addition to providing the status information as described above, the user interface 500 additionally includes an indicator applied to entries in the table when a software and/or configuration update is available. For example, indicator 508 can be applied to a location when a software update is available for one or more units of medical equipment associated with the location. A user can see additional information about the available software updates by selecting the location to see device level information (e.g., as shown in FIG. 3B). Additionally, and/or alternatively update information could be included in an additional column of the table.

In some examples, user interface 500 can additionally allow a user to update a the software and/or configurations for the medical equipment. In order to update the software for the devices associated with a particular location, and administrator can select the update all link 510. If the administrator would prefer to update the devices individually, and update link can be included on the device specific status page. Selection of the software update link sends available updates to the medical equipment.

Figure 6:
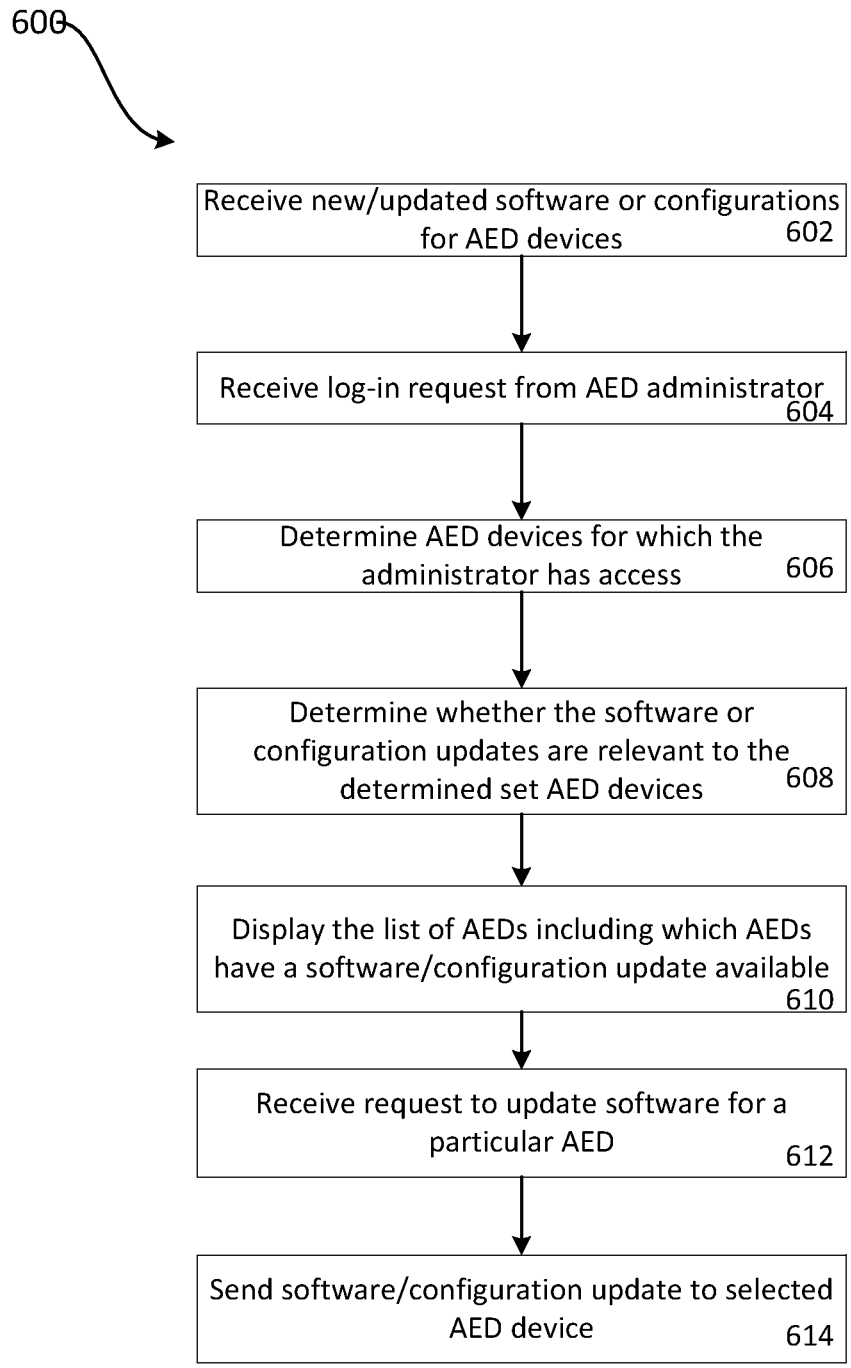
FIG. 6 is a flow chart of a process for providing software and/or configuration updates to medical equipment according to an example embodiment of the invention.

FIG. 6 is a flow chart of a process 600 for providing software and/or configuration updates to automated external defibrillators (AEDs). While process 600 is described herein as providing status information and updating AEDs, this process could additionally and/or alternatively be applied to other types of medical equipment. Process 600 begins with the receipt of new or updated software and/or configurations for AEDs (602). For example, changes to configurations or updates to software can be stored in a central database. The medical equipment management system 216 receives a login request from an AED administrator (604).

Based on the authentication of the administrator, the medical equipment management system 216 determines AED devices for which the administrator should be granted access (606). For example, in the database that includes the information about the AEDs and their status, each AED may be associated with one or more administrators who are allowed access to the status of the AEDs and push updates to the AEDs. For the devices identified as being associated with the administrator, the medical equipment management system determines whether the software and/or configuration updates are relevant to the determined set of AEDs. For example, current configurations or software versions for the AEDs can be compared to a list of available updates to see if the most recent configurations and software are stored on the AEDs. The software and configurations available for a particular AED may be based on a make or model of the AED. For example, some software updates may only be available to a subset of AED models. In some examples, software updates and configuration updates can be associated with model numbers and with a timestamp of when the software update or configuration update was provided. Using this information, stored device models and a time of the last update for a particular device can be used to determine whether configuration or software updates are available for the device. The medical equipment management system 216 displays to the user, a list of AEDs including which AEDs have software and/or configuration updates available. For example, the medical equipment management system 212 can send information to a user device to cause the user device to display such a list. The list can be grouped by location, for example, as described above. A user can update the software or configurations on one or more of the AEDs by selecting a link to send the update to the AED. Based on the user entered request for update, the medical equipment management system 212 receives the request to update software, and/or configurations for a particular AED (not shown) or for all AEDs associated with a particular location (612). Based on the received request, the medical equipment management system 212 sends the software and/or configuration update to the selected AED device or group of AED devices (614). Thus, the administrator can update the software and/or configurations for a particular AED device or group of AED devices from a central location.

Figure 7:
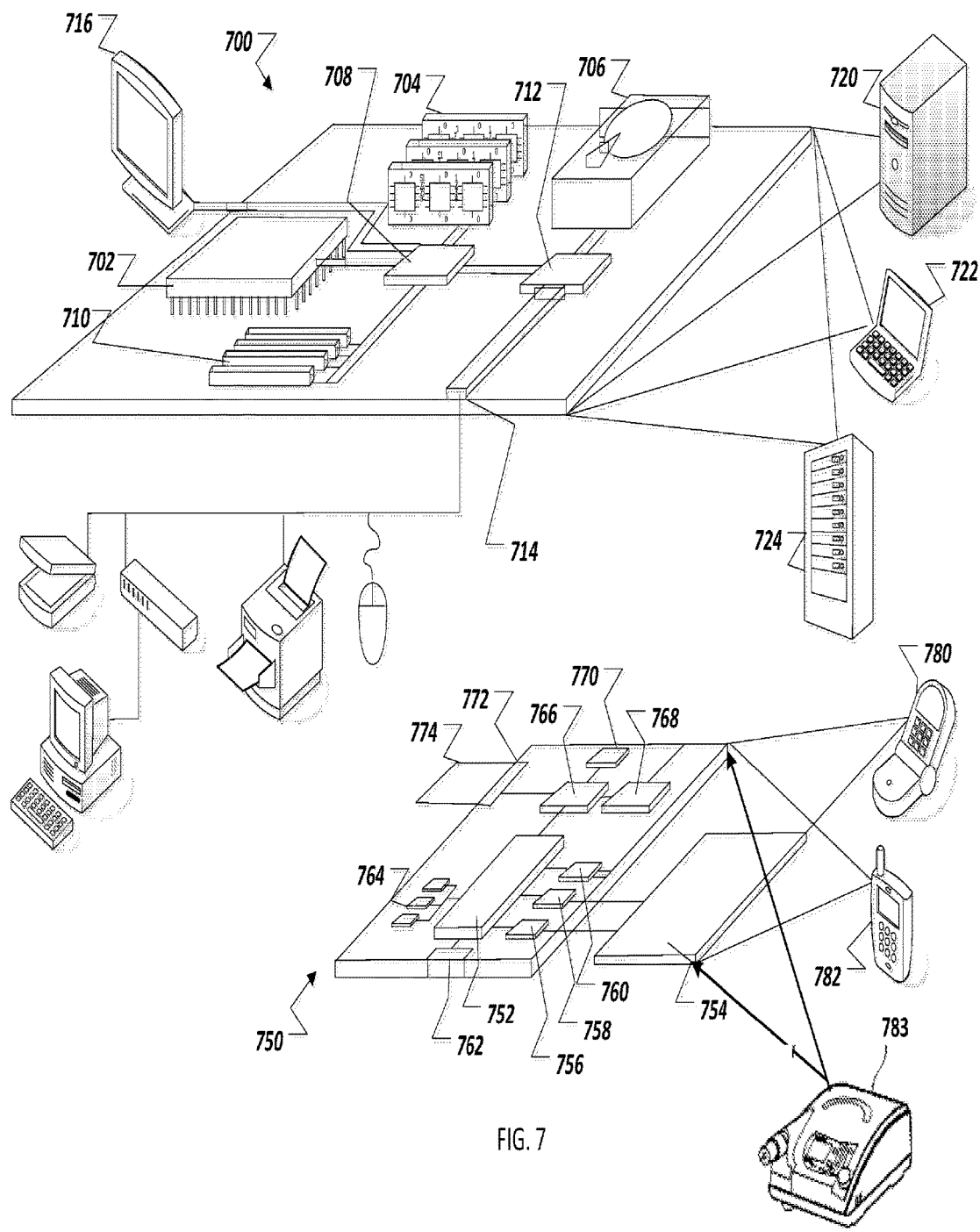
FIG. 7 shows an example of a generic computer device and a generic mobile computer device, which may be used with the techniques described herein.

FIG. 7 shows an example of a generic computer device 700 and a generic mobile computer device 750, which may be used with the techniques described here. Generic computer device 700 can be used to provide the above described functionality of the medical equipment management system 212. Computing device 700 is intended to represent various forms of digital computers, such as laptops, desktops, workstations, personal digital assistants, servers, blade servers, mainframes, and other appropriate computers. Generic mobile computer device 750 can be a computing component of defibrillator 112 or can be a laptop computer such as laptop computer 116. Computing device 750 is intended to represent various forms of mobile devices, such as personal digital assistants, cellular telephones, smartphones, and other similar computing devices that can receive information from a defibrillator 112 and provide that information to another computing device such as computer device 700. The components shown here, their connections and relationships, and their functions, are meant to be exemplary only, and are not meant to limit implementations of the inventions described and/or claimed in this document.

Computing device 700 includes a processor 702, memory 704, a storage device 706, a high-speed interface 708 connecting to memory 704 and high-speed expansion ports 710, and a low speed interface 712 connecting to low speed bus 714 and storage device 706. Each of the components 702, 704, 706, 708, 710, and 712, are interconnected using various busses, and may be mounted on a common motherboard or in other manners as appropriate. The processor 702 can process instructions for execution within the computing device 700, including instructions stored in the memory 704 or on the storage device 706 to display graphical information for a GUI on an external input/output device, such as display 716 coupled to high speed interface 708. In other implementations, multiple processors and/or multiple buses may be used, as appropriate, along with multiple memories and types of memory. Also, multiple computing devices 700 may be connected, with each device providing portions of the necessary operations (e.g., as a server bank, a group of blade servers, or a multi-processor system).

The memory 704 stores information within the computing device 700. In one implementation, the memory 704 is a volatile memory unit or units. In another implementation, the memory 704 is a non-volatile memory unit or units. The memory 704 may also be another form of computer-readable medium, such as a magnetic or optical disk.

The storage device 706 is capable of providing mass storage for the computing device 700. In one implementation, the storage device 706 may be or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product may also contain instructions that, when executed, perform one or more methods, such as those described above. For example, the computer program product may contain instructions for receiving status information from and displaying status information for various medical devices such as AEDs. The information carrier is a computer- or machine-readable medium, such as the memory 704, the storage device 706, or memory on processor 702.

The high speed controller 708 manages bandwidth-intensive operations for the computing device 700, while the low speed controller 712 manages lower bandwidth-intensive operations. Such allocation of functions is exemplary only. In one implementation, the high-speed controller 708 is coupled to memory 704, display 716 (e.g., through a graphics processor or accelerator), and to high-speed expansion ports 710, which may accept various expansion cards (not shown). In the implementation, low-speed controller 712 is coupled to storage device 706 and low-speed expansion port 714. The low-speed expansion port, which may include various communication ports (e.g., USB, Bluetooth, Ethernet, wireless Ethernet) may be coupled to one or more input/output devices, such as a keyboard, a pointing device, a scanner, or a networking device such as a switch or router, e.g., through a network adapter.

The computing device 700 (e.g., management system 216) may be implemented in a number of different forms, as shown in the figure. For example, it may be implemented as a standard server 720, or multiple times in a group of such servers. It may also be implemented as part of a rack server system 724. In addition, it may be implemented in a personal computer such as a laptop computer 722. Alternatively, components from computing device 700 may be combined with other components in a mobile device (not shown), such as device 750. Each of such devices may contain one or more of computing device 700, 750, and an entire system may be made up of multiple computing devices 700, 750 communicating with each other.

Computing device 750 provides information about the status of medical equipment such as an AED to management system 216 (e.g., to computing device 700) and includes a processor 752, memory 764, and an input/output device such as a display 754, a communication interface 766, and a transceiver 768, among other components. The device 750 may also be provided with a storage device, such as a microdrive or other device, to provide additional storage. Each of the components 750, 752, 764, 754, 766, and 768, are interconnected using various buses, and several of the components may be mounted on a common motherboard or in other manners as appropriate. In some examples, computing device 750 is included in an AED such as AED 112 shown in FIG. 1.

The processor 752 can execute instructions within the computing device 750, including instructions stored in the memory 764. For example, the processor 752 can execute instructions to perform a self-test on a piece of medical equipment and forward the results to the central management system 216. The processor may be implemented as a chipset of chips that include separate and multiple analog and digital processors. The processor may provide, for example, for coordination of the other components of the device 750, such as control of user interfaces, applications run by device 750, and wireless communication by device 750.

Processor 752 may communicate with a user through control interface 758 and display interface 756 coupled to a display 754. The display 754 may be, for example, a TFT LCD (Thin-Film-Transistor Liquid Crystal Display) or an OLED (Organic Light Emitting Diode) display, or other appropriate display technology. The display interface 756 may comprise appropriate circuitry for driving the display 754 to present graphical and other information to a user. The control interface 758 may receive commands from a user and convert them for submission to the processor 752. In addition, an external interface 762 may be provide in communication with processor 752, so as to enable near area communication of device 750 with other devices. External interface 762 may provide, for example, for wired communication in some implementations, or for wireless communication in other implementations, and multiple interfaces may also be used.

The memory 764 stores information within the computing device 750. The memory 764 can be implemented as one or more of a computer-readable medium or media, a volatile memory unit or units, or a non-volatile memory unit or units. Expansion memory 774 may also be provided and connected to device 750 through expansion interface 772, which may include, for example, a SIMM (Single In Line Memory Module) card interface. Such expansion memory 774 may provide extra storage space for device 750, or may also store applications or other information for device 750. Specifically, expansion memory 774 may include instructions to carry out or supplement the processes described above, and may include secure information also. Thus, for example, expansion memory 774 may be provide as a security module for device 750, and may be programmed with instructions that permit secure use of device 750. In addition, secure applications may be provided via the SIMM cards, along with additional information, such as placing identifying information on the SIMM card in a non-hackable manner.

The memory may include, for example, flash memory and/or NVRAM memory, as discussed below. In one implementation, a computer program product is tangibly embodied in an information carrier. The computer program product contains instructions that, when executed, perform one or more methods, such as those described above. The information carrier is a computer- or machine-readable medium, such as the memory 764, expansion memory 774, or memory on processor 752.

Device 750 may communicate wirelessly through communication interface 766, which may include digital signal processing circuitry where necessary. Communication interface 766 may provide for communications under various modes or protocols, such as GSM voice calls, SMS, EMS, or MMS messaging, CDMA, TDMA, PDC, WCDMA, CDMA2000, or GPRS, among others. Such communication may occur, for example, through radio-frequency transceiver 768. In addition, short-range communication may occur, such as using a Bluetooth, WiFi, or other such transceiver (not shown). In addition, GPS (Global Positioning System) receiver module 770 may provide additional navigation- and location-related wireless data to device 750, which may be used as appropriate by applications running on device 750. This communication via communication interface 766 can provide status information about the associated medical equipment to the management system 216 (e.g., to computing device 700).

Device 750 may also communicate audibly using audio codec 760, which may receive spoken information from a user and convert it to usable digital information. Audio codec 760 may likewise generate audible sound for a user, such as through a speaker, e.g., in a handset of device 750. Such sound may include sound from voice telephone calls, may include recorded sound (e.g., voice messages, music files, etc.) and may also include sound generated by applications operating on device 750.

The computing device 750 may be implemented in a number of different forms, as shown in the figure. For example, it may be implemented as a cellular telephone 780. It may also be implemented as part of a, personal digital assistant, or other similar mobile device. It may also be implemented as part of a AED 783, or other medical equipment. It may also be implemented as part of a laptop computer such as computer 116 in FIG. 1.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" "computer-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

A number of embodiments have been described. Nevertheless, it will be understood that various modifications may be made without departing from the spirit and scope of the invention.

In addition, the logic flows depicted in the figures do not require the particular order shown, or sequential order, to achieve desirable results. In addition, other steps may be provided, or steps may be eliminated, from the described flows, and other components may be added to, or removed from, the described systems. Accordingly, other embodiments are within the scope of the following claims. Many other implementations of the invention other than those described above are within the invention, which is defined by the following claims.

What is claimed is:

1. A medical equipment management system comprising:
   a database comprising software for a plurality of external defibrillators, the software comprising at least one of new software and updated software; and
   a computer located remotely from the plurality of external defibrillators and configured to be communicatively coupled to the plurality of external defibrillators via a cellular network and to:
      receive a login request from an administrator,
      based on the login request, determine from amongst the plurality of external defibrillators in the database a set of external defibrillators associated with the administrator,
      determine whether the software stored in the database is relevant to the set of external defibrillators associated with the administrator, and
      send the relevant software to the set of external defibrillators associated with the administrator.

2. The system of claim 1, wherein the computer is configured to group the set of external defibrillators according to location.

3. The system of claim 1, wherein the computer is configured to receive a request for the at least one of new software and updated software available for the set of external defibrillators.

4. The system of claim 1, wherein the set of external defibrillators comprises all of a group of external defibrillators associated with a particular location.

5. The system of claim 1 wherein the plurality of external defibrillators is a plurality of automated external defibrillators.

6. A medical equipment management system comprising:
   a database comprising a configuration for a plurality of external defibrillators, the configuration comprising at least one of a new configuration and an updated configuration; and
   a computer located remotely from the plurality of external defibrillators and configured to be communicatively coupled to the plurality of external defibrillators via a cellular network and to:
      receive a login request from a administrator,
      based on the login request, determine, from amongst the plurality of external defibrillators in the database, a set of external defibrillators associated with the administrator,
      determine whether the configuration stored in the database is relevant to the set of external defibrillators associated with the administrator, and
      send the relevant configuration to the set of external defibrillators associated with the administrator.

7. The system of claim 6, wherein the computer is configured to group the set of external defibrillators according to location.

8. The system of claim 6, wherein the computer is configured to receive a request for the at least one of the new configuration and the updated configuration available for the set of external defibrillators.

9. The system of claim 6, wherein the set of external defibrillators comprises all of a group of external defibrillators associated with a particular location.

10. The system of claim 6 wherein the plurality of external defibrillators is a plurality of automated external defibrillators.

11. The system of claim 6 wherein the configuration comprises one or more of a language setting, a CPR parameter, and a defibrillation shock parameter.

12. A medical equipment management system comprising:
    a database comprising software for a plurality of external defibrillators, the software comprising at least one of new software and updated software; and
    a computer located remotely from the plurality of external defibrillators and configured to be communicatively coupled to the plurality of external defibrillators via a Wi-Fi network and to:
       receive a login request from an administrator,
       based on the login request, determine from amongst the plurality of external defibrillators in the database a set of external defibrillators associated with the administrator,
       determine whether the software stored in the database is relevant to the set of external defibrillators associated with the administrator, and
       send the relevant software to the set of external defibrillators associated with the administrator.

13. The system of claim 12, wherein the computer is configured to group the set of external defibrillators according to location.

14. The system of claim 12, wherein the computer is configured to receive a request for the at least one of new software and updated software available for the set of external defibrillators.

15. The system of claim 12, wherein the set of external defibrillators comprises all of a group of external defibrillators associated with a particular location.

16. The system of claim 12 wherein the plurality of external defibrillators is a plurality of automated external defibrillators.

17. A medical equipment management system comprising:
- a database comprising a configuration for a plurality of external defibrillators, the configuration comprising at least one of a new configuration and an updated configuration; and
- a computer located remotely from the plurality of external defibrillators and configured to be communicatively coupled to the plurality of external defibrillators via a Wi-Fi network and to:
  - receive a login request from a administrator,
  - based on the login request, determine, from amongst the plurality of external defibrillators in the database, a set of external defibrillators associated with the administrator,
  - determine whether the configuration stored in the database is relevant to the set of external defibrillators associated with the administrator, and
  - send the relevant configuration to the set of external defibrillators associated with the administrator.

18. The system of claim 17, wherein the computer is configured to group the set of external defibrillators according to location.

19. The system of claim 17, wherein the computer is configured to receive a request for the at least one of the new configuration and the updated configuration available for the set of external defibrillators.

20. The system of claim 17, wherein the set of external defibrillators comprises all of a group of external defibrillators associated with a particular location.

21. The system of claim 17 wherein the plurality of external defibrillators is a plurality of automated external defibrillators.

22. The system of claim 17 wherein the configuration comprises one or more of a language setting, a CPR parameter, and a defibrillation shock parameter.

23. A medical equipment management system comprising:
- a database comprising a configuration for a plurality of external defibrillators, the configuration comprising at least one of a new configuration and an updated configuration; and
- a computer located remotely from the plurality of external defibrillators and configured to be communicatively coupled to the plurality of external defibrillators and to:
  - receive a login request from a administrator,
  - based on the login request, determine, from amongst the plurality of external defibrillators in the database, a set of external defibrillators associated with the administrator,
  - determine whether the configuration stored in the database is relevant to the set of external defibrillators associated with the administrator, and
  - send the relevant configuration to the set of external defibrillators associated with the administrator,
  - wherein the configuration comprises one or more of a language setting, a CPR parameter, and a defibrillation shock parameter.

24. The system of claim 23, wherein the computer is configured to group the set of external defibrillators according to location.

25. The system of claim 23, wherein the computer is configured to receive a request for the at least one of the new configuration and the updated configuration available for the set of external defibrillators.

26. The system of claim 23, wherein the set of external defibrillators comprises all of a group of external defibrillators associated with a particular location.

27. The system of claim 23 wherein the plurality of external defibrillators is a plurality of automated external defibrillators.

28. The system of claim 23 wherein the computer is configured to be communicatively coupled to the plurality of external defibrillators via a cellular network.

29. The system of claim 23 wherein the computer is configured to be communicatively coupled to the plurality of external defibrillators via a Wi-Fi network.

* * * * *

UNITED STATES PATENT AND TRADEMARK OFFICE
CERTIFICATE OF CORRECTION

| | | |
|---|---|---|
| PATENT NO. | : 10,258,806 B2 | Page 1 of 1 |
| APPLICATION NO. | : 15/957946 | |
| DATED | : April 16, 2019 | |
| INVENTOR(S) | : Ziad F. Elghazzawi, Ian B. Durrant and Henry Clay Constantine, III | |

It is certified that error appears in the above-identified patent and that said Letters Patent is hereby corrected as shown below:

In the Specification

Column 3, Line 22, delete "12/946,843", insert -- 12/946,803 --

Signed and Sealed this
Fourth Day of July, 2023

Katherine Kelly Vidal
*Director of the United States Patent and Trademark Office*